US010201563B2

(12) United States Patent
Alliger

(10) Patent No.: US 10,201,563 B2
(45) Date of Patent: Feb. 12, 2019

(54) METHOD OF TREATING SINUSITIS, INCLUDING CHRONIC SINUSITIS

(71) Applicant: Howard M. Alliger, Melville, NY (US)

(72) Inventor: Howard M. Alliger, Melville, NY (US)

(73) Assignee: SINOX PHARMA, INC., Topanga, CA (US)

( * ) Notice: Subject to any disclaimer, the term of this patent is extended or adjusted under 35 U.S.C. 154(b) by 0 days.

(21) Appl. No.: 14/952,221

(22) Filed: Nov. 25, 2015

(65) Prior Publication Data

US 2016/0074432 A1 Mar. 17, 2016

Related U.S. Application Data

(63) Continuation of application No. 13/522,570, filed as application No. PCT/US2011/021524 on Jan. 18, 2011, now abandoned.

(60) Provisional application No. 61/336,319, filed on Jan. 19, 2010, provisional application No. 61/372,233, filed on Aug. 10, 2010.

(51) Int. Cl.

| A61K 9/00 | (2006.01) |
|---|---|
| A61K 31/09 | (2006.01) |
| A61K 33/00 | (2006.01) |
| A61K 33/20 | (2006.01) |
| A61K 45/06 | (2006.01) |
| A61K 31/047 | (2006.01) |

(52) U.S. Cl.
CPC .............. *A61K 33/00* (2013.01); *A61K 9/006* (2013.01); *A61K 9/0043* (2013.01); *A61K 31/047* (2013.01); *A61K 31/09* (2013.01); *A61K 33/20* (2013.01); *A61K 45/06* (2013.01)

(58) Field of Classification Search
CPC ...... A61K 9/0043; A61K 9/006; A61K 33/00; A61K 33/20
See application file for complete search history.

(56) References Cited

U.S. PATENT DOCUMENTS

| 4,084,747 | A | 4/1978 | Alliger | |
|---|---|---|---|---|
| 5,651,996 | A | 7/1997 | Roozdar | |
| 6,017,554 | A | 1/2000 | Ratcliff | |
| 6,039,934 | A | 3/2000 | Alliger | |
| 2002/0197215 | A1* | 12/2002 | Stier | A61K 8/22 424/53 |
| 2004/0071788 | A1* | 4/2004 | Fuhr | A61K 33/06 424/661 |
| 2005/0142157 | A1* | 6/2005 | Alimi | A01N 59/00 424/405 |
| 2007/0196434 | A1 | 8/2007 | Alimi et al. | |

FOREIGN PATENT DOCUMENTS

| EP | 2133083 A1 | 12/2009 |
|---|---|---|
| EP | 2147676 A1 | 1/2010 |
| WO | 8903179 A1 | 4/1989 |

OTHER PUBLICATIONS

Ma et al., "Efficacy and Safety Evaluation of a Chlorine Dioxide Solution", 2017, International Journal of Environmental Research and Public Health, vol. 14, pp. 329-340. (Year: 2017).*
Chan Y, et al. An update on the classifications, diagnosis, and treatment of rhinosinusitis. Current Opinion in Otolaryngology & Head and Neck Surgery, 2009;17(3):204-208.
Hamilos DL. Chronic Sinusitis. The Journal of Allergy and Clinical Immunology, 2000;106(2):213-227.

* cited by examiner

*Primary Examiner* — Michael B. Pallay
(74) *Attorney, Agent, or Firm* — Henry D. Coleman; R. Neil Sudol

(57) ABSTRACT

The present application discloses a method for treating acute and chronic sinusitis, and in particular, severe chronic sinusitis by exposing affected tissue of the sinus and contiguous tissue in the, nasal cavity and greater oral cavity to effective amounts of chlorine dioxide as a bioactive agent. Compositions and methods of treatment are disclosed herein.

28 Claims, No Drawings

METHOD OF TREATING SINUSITIS, INCLUDING CHRONIC SINUSITIS

RELATED APPLICATIONS

This application is a continuation application of United States national phase patent application Ser. No. 13/522,570 filed Dec. 18, 2012, which is a United States national phase patent application based upon International Patent Application No. PCT/US2011/021524 filed 18 Jan. 2011 entitled "A Method of Treating Sinusitis, Including Chronic Sinusitis", which claims the benefit of priority of U.S. provisional application No. US61/336,319, filed Jan. 19, 2010 entitled "Use of Chlorine Dioxide Solutions for Treatment of Sinusitis and Other Inflammatory Conditions of the Nasal, Oral and Sinus Cavities", and US61/372,233, filed Aug. 10, 2010, entitled "A Method of Treating Sinusitis and Rhinitis, Including Chronic Sinusitis and Other Upper Respiratory Tract Conditions", all four of which applications are incorporated by reference in their entirety herein.

FIELD OF THE INVENTION

The present invention relates to a method for treating acute and chronic sinusitis, and in particular, severe chronic sinusitis by exposing affected tissue of the sinus and greater oral cavity to effective amounts of chlorine dioxide as a bioactive agent. Compositions and methods of treatment are disclosed herein.

BACKGROUND OF THE INVENTION

Rhinosinusitis is one of the most diagnosed diseases in the U.S., responsible for nearly $5.8 billion annually in health care costs. Chronic, and recurrent acute sinusitis, can be a lifelong condition and difficult to treat. The illness can also set the stage for bronchitis and pneumonia, especially in the elderly, since the microorganisms are often the same. Because disease and inflammation in the greater oral cavity are interrelated, the general condition is sometimes known by researchers and specialists in the field as "chronic rhinosinusitis."

Sinusitis refers to an inflammation of the sinuses or airspaces within the bones of the face. Many times this flare-up is acute when caused by infection within these spaces, but continuous irritation may lead to swelling and obstruction, providing a conducive environment for microorganism growth. The ensuing infection in the nose is almost always bacterial. Typically the process starts with a cold virus (there are over 200 kinds) in the nasal cavities, causing brief and mild inflammation, often referred to as rhinitis. A cold or flu virus, however, can also create a more onerous condition by producing greater inflammation and congestion in nasal passages. As the duration and severity of this initial infection grows, the likelihood of related and chronic conditions increase, affecting the health anywhere in the entire respiratory tract. The resulting illness may be bacterial, viral or fungal (10), and also due to allergy or immune response. Roughly 90% of adults have had sinusitis at some point in their lives (2), and chronic sinusitis and rhinitis is more common than any other chronic condition (1).

According to the *Journal of Allergy and Immunology*, 2000, "Unfortunately, sinusitis is often very frustrating and difficult to treat, and medical failures often become surgical patients." "There were approximately 200,000 sinus surgeries in the United States in 1994."—"No hypothesis explains the complex interplay of infectious and inflammatory stimuli that contribute to the disease. There is also a great need for improved therapies to combat this frustrating chronic illness." In a more recent approach, according to the book *Sinus Relief Now*, 2006, by Josephson, "We now believe that the inflammatory process affecting, the nose, the sinuses, and the lungs is one and the same process."—"The membranes that line the nose, sinuses, and lungs, are so sensitive, that inflammation in any of these areas can ultimately affect the others." The entire respiratory tract is lined with the same skin (7), and an infection or inflammation that occurs in the nose can travel to the lungs (23).

Although the onset and enduring nature of chronic sinusitis has many facets, I have discovered an easy to administer procedure, and the use of a narrow concentration range of chlorine dioxide that will halt the onset of the illness or its aftermath. This invention will also reduce or completely relieve the battery of familiar cold symptoms, and in most cases eliminate the cause of the problem whether infectious or immune triggered.

In 1978 the inventor of the present application received the first patent (U.S. Pat. No. 4,084,747) for applying chlorine dioxide disinfectant to the body for treating infection and disease. The patent since that time has spawned approximately 200 patents by others, incorporating $ClO_2$ for topical use. Since 1978, a number of products for use on human and animal diseases utilizing chlorine dioxide have been created.

A number of compounds such as chlorhexidine, hydrogen peroxide, Triclosan, cetylperdinium chloride, iodophors, quaternary ammonium compounds and household bleach have been used as disinfectants. Because of the great need to disinfect the mouth, however, these same disinfectants are often used in oral preparations for odor or bacteria removal, and after dental procedures. They taste bad and have other limitations, and the most effective, chlorhexidine, causes significant staining of the teeth as well as suppressing taste receptors. Moreover, chlorhexidine, a relatively effective antiseptic cannot be used on the more serious gum disease, periodontitis, because of its burning effect on tissue, especially open sores. Hydrogen peroxide, one of the most common antiseptics, is considered highly irritating on mucus membranes. Many topical disinfectants are not very effective on *pseudomonas*, for example, or many other gram negative bacteria. An example of these include iodine compounds like Betadyne, often used on the skin. Common topical disinfectants like Triclosan and quaternary ammonium compounds are slow acting and are poor inactivators of most viruses and spores.

A broad spectrum antimicrobial property is vital for treating chronic sinusitis which harbors an array of organisms, including *Streptococcus pneumoniae, Hemophilus influenzae, Moraxella catarrhalis, Staphylococcus aureus*, and anaerobic bacteria, *Fusobacterium, Prevotella, Porphyromonas*, and *Peptostreptococcus*, and finally, fungi, *Alternaria, Aspergillus, Penicillium, Cladosporiuim*, and *Candida*. The Mayo Clinic, found fungi in 96% of people with chronic sinusitis. Elsewhere it was shown that 90% of people that had nasal congestion for more than a year had positive cultures of *Chlamydia pneumoniae* (12). Many microbes become resistant to antibiotics, or are not responsive to them at all. It is of interest as well, that most potential virucides are cytotoxic, even at very small concentrations (Chemical Inactivation, by Arana-Anzaldo).

With all of various $ClO_2$ treatments discovered over the last 25 year period by the present inventor and others, the most surprising is the present discovery that $ClO_2$ is useful for treating and curing colds, sore throats, sinusitis and most importantly chronic sinusitis. All of these conditions are related. Over 85% of people with colds, for example, have inflamed sinuses, sometimes called rhinitis. The various conditions are also caused by the same microorganisms and display many of the same symptoms. Sinusitis is usually triggered by a cold or sore throat, but sinusitis in turn can develop into bronchitis, or throat irritation. According to a National Institute of Allergy and Infectious Diseases Bulletin, "Scientific studies have shown a close relationship between having asthma and sinusitis. For example, the vast majority of people with moderate to severe asthma also have chronic sinusitis."

OBJECTS OF THE INVENTION

It is an object of the invention to provide a treatment of sinusitis, especially chronic sinusitis.

It is another object of the invention to provide a method which reduces the likelihood of sinusitis in those individuals who are at risk for sinusitis, especially those with asthma and the elderly.

It is still another object of the invention to provide compositions which can be applied in several ways to reduce inflammation and infection in the nasal, oral and sinus cavities, resulting in a particularly useful for the treatment and/or inhibition of sinusitis.

It is still yet another object of the invention to provide chlorine dioxide containing compositions which exhibit stable chlorine dioxide levels for a period of at least 1 day or more.

It is yet an additional object of the invention to provide a method to relieve symptoms of sinusitis including congestion, headache, clearing of mucus, coughing and pain.

It is another object of the invention to provide a method for treating colds and/or sore throats which are precursors to sinusitis in the same tissues in a patient in need.

Any one or more of these and/or other objects of the invention may be readily gleaned from a review of the description of the invention which follows.

SUMMARY OF THE INVENTION

The present invention relates to the use of chlorine dioxide containing solutions which are useful in the treatment or inhibition of sinusitis, especially chronic sinusitis in subjects or patients who have sinusitis or are at risk for sinusitis. In the present invention, an effective amount of chlorine dioxide is delivered to the tissues within or surrounding the sinus cavities of a patient or subject ("patient at risk") who is suffering from sinusitis, especially including chronic sinusitis or who is at risk for sinusitis, for example, as a consequence of having allergies, asthma or being elderly and more at risk for sinusitis.

The present invention also contemplates the administration of effective amounts of chlorine dioxide to the sinus and surrounding tissue of a patient to reduce the likelihood of sinusitis, especially chronic sinusitis. In this method a composition comprising an effective amount of chlorine dioxide is administered as otherwise disclosed herein to the sinus and surrounding tissues including the roof and back of the mouth and throat of the patient or subject in order to inhibit or otherwise reduce the likelihood of sinusitis, including chronic sinusitis and throat infections such as tonsillitis from occurring. This method is particularly advantageous to allergy and asthma sufferers, as well as the elderly and other individuals prone to sinusitis. In alternative embodiments, the tissue of the nasal passages and throat tissues (in addition to sinus tissues and tissues contiguous to sinus tissues) are also exposed to effective concentrations of chlorine dioxide in the present method, thus reducing the likelihood that a cold or sore throat would result in the recurrence of sinusitis after treatment.

Compositions according to the present invention can be presented in two parts, i.e., an acid part and a chlorite salt part, such that when the two part composition is mixed, chlorine dioxide is produced. The mixed composition is administered to a patient as an oral or nasal spray, an aerosol, as steam, as vapor (e.g., from a humidifier), as nose drops, as a liquid lavage, as a mouthwash, among other formulations or methods of administration. In order to enhance formation of chlorine dioxide, a disproportionation agent in effective amounts as otherwise disclosed herein may also be added to acid part or chlorite part, depending upon the stability of the disproportionation agent in acid or base conditions. In alternative embodiments, the chlorine dioxide may be presented in a single composition, as stabilized chlorine dioxide. In addition to effective amounts of chlorine dioxide, the compositions which are used to treat and/or inhibit sinusitis (including reducing the likelihood of sinusitis and/or chronic sinusitis) may contain additional components which are particularly adapted for improving the condition of the sinus membranes and surrounding tissue.

In certain preferred embodiments according to the present invention, in order to maintain the substantially same concentration (i.e., not falling outside of a range) of $ClO_2$ within the range of about 10 ppm to about 20 ppm from the first few seconds up to about a minute or so after the initial formation of chlorine dioxide for up to 2 or 3 days, the composition comprises a carbohydrate, including a sugar such as ribose and a hydroxyl free aldehyde such as cinnamic aldehyde in combination as a disproportionation agent, sodium chlorite and acid to provide a pH within the range of about 5.5 to about 6.5, preferably at a pH of about 6.0. In preferred aspects ribose is included in said composition at a weight ratio of about 0.05% to about 0.1% by weight, preferably about 0.075% by weight; cinnamic aldehyde is included in an amount ranging from about 0.05% to about 0.15% by weight, preferably about 0.1% by weight, chlorite is included in an amount ranging from about 0.1% to about 0.3%, preferably about 0.2% and the pH of the composition ranges from about 5.0 to about 6.5, preferably about 5.5 to about 6.5, preferably about 5.0 to about 6.0. In this aspect of the invention, the rate of $ClO_2$ loss through evaporation from these compositions must be equal to the $ClO_2$ production which occurs from combining the ingredients. In this case, also, the solution is held preferably in a small spray bottle. Because of this level concentration, the same bottle and ingredients use will be safe and effective over a several day use, and perhaps more importantly, over the first 10 or 20 minutes, when the solution is gargled or added to the nose and/or sinuses several times within that period. A preferred concentration of about 10-20 ppm, about 14-17, about 16 ppm $ClO_2$ is ideal for nose, throat and sinus infections for eliminating the infection without undo stinging or discomfort when applied to the wounded tissue of the oral cavity. A level of $ClO_2$ of about 15-16 ppm can be maintained by the following concentration of active ingredients: 0.075% ribose, 0.1% cinnamon aldehyde, 0.2% sodium chlorite, and a pH between about 5.5 and 6.5 for a period up to 2-3 days.

DETAILED DESCRIPTION OF THE INVENTION

The term "patient" or "subject" is used to describe an animal, preferably a mammalian animal including a domesticated animal, and especially a human patient to whom therapy according to the present invention is applied. The term "patient at risk" or "subject at risk" describes a patient or subject, because of having certain conditions or diseases or being exposed to conditions as otherwise described herein, create an elevated risk of sinusitis and/or chronic sinusitis in that patient or subject.

The term "effective" is used to describe an amount of chlorine dioxide or other component which is used in a composition according to the present invention or method as described herein to produce an intended result, especially including treating or inhibiting sinusitis or reducing the likelihood that a patient or subject at risk for sinusitis contracts sinusitis. In preferred aspects of the invention, an effective amount of chlorine dioxide ranges from about 1 ppm (parts per million) to about 100 ppm, preferably about 2 ppm to about 50 ppm, about 5 to about 30 ppm, about 5 to about 25 ppm, about 7.5 to about about 20 ppm of chlorine dioxide, about 10 to about 20 ppm of chlorine dioxide, about 15 to about 25 ppm of chlorine dioxide.

The term "acid" is used throughout the specification to describe protic acids, i.e., acids that release hydrogen ions in solution and combine with a chlorite salt in certain aspects of the invention in producing effective amounts of chlorine dioxide for use in treating or reducing the likelihood of the occurrence of sinusitis, in particular, chronic sinusitis, as otherwise described herein. Acids for use in the present invention may include inorganic acids such as hydrochloric, sulfuric, sulfamic and nitric acid, preferably as dilute acid or organic acids such as citric, fumaric, glycolic, lactic, malic, and tartaric acid, among others, additional acids such as sodium and potassium bisulfate, phosphoric acid and maleic acid. Preferred acids for generating chlorine dioxide include, for example an α-hydroxy acid selected from the group consisting of lactic, citric, glycolic, malic, tartaric, mandelic and mixtures thereof, with lactic acid or a mixture of lactic acid and an additional acid being especially preferred.

The term "salt of a chlorite" or "chlorite salt" is used throughout the specification to describe a salt of chlorite which is readily soluble in an aqueous system and which readily dissociates into chlorite anion and counterion (generally, metal). Two particularly preferred salts of chlorites for use in the present invention include sodium chlorite and potassium chlorite, although other salts of chlorite may also be used in the present invention.

The term "disproportionation agent" is used throughout the specification to describe a compound which enhances the formation of chlorine dioxide from a combination of an acid and chlorite salt as otherwise described herein. Disproportionation agents for use in the present invention are used to enhance the rate of disproportionation and significantly increase the amount of chlorine dioxide which is produced from a combination of acid and chlorite and minimize the residual chlorite ion. Disproportionation agents for use in the present invention are chosen for their ability to substantially enhance the rate and efficiency (yield) at which chlorine dioxide is formed, for their ability to form biologically compatible substantially non-toxic organic acid side products and for their ability to minimize residual chlorite ion which are found in the compositions. Thus, by using a disproportionation agent in compositions according to the present invention, one can produce effective quantities of chlorine dioxide, minimize the amount of acid used and raise the pH of the chlorite generating to reflect pharmaceutical compatability.

Where used, disproportionation agents for use in the present invention preferably include hydroxyl free aldehydes, most preferably, non-toxic hydroxyl free aldehydes such as acetaldehyde, benzaldehyde, glutaraldehyde, cinnamic aldehyde, propionaldehyde, paraldehyde and 2-Furfural (bran oil), among others. Additional disproportionation agents, although less preferred, include, for example, sugars such as ribose, glucose (dextrose), galactose, fructose, etc. which can exist in equilibrium as aldose forms, in which form it is believed that disprotionation occurs.

Preferred disproportionation agents for use in the present invention include those aldehydes that are substantially non-toxic themselves and which are converted during the disprotionation process to non-toxic side products. The hydroxyl free aldehydes acetaldehyde, benzaldehyde, glutaraldehyde, cinnamic aldehyde (cinnamon aldehyde) and propionaldehyde are preferred for use in the present invention, and less preferred are the sugars, including ribose, glucose, galactose and fructose. Pursuant to the present invention, the use of these disproportionation agents is compatible with sinus tissue and minimizes irritation of the sinus and contiguous tissues.

The term "hydroxyl free aldehyde" is used throughout the specification to describe certain disproportionation agents for use in the present invention. Hydroxyl free aldehydes are those chemical compounds containing an aldehyde moiety which is free of hydroxyl groups. These disproportionation agents, where a disproportionation agent is used, are preferred for use in the present invention. Also used in certain instances, although less preferably, are sugars, especially monomeric sugars such as ribose, fructose, glucose (dextrose) and galactose, among others, preferablyi ribose. The inclusion of a disproportionation agent (preferably a hydroxyl free aldehyde as otherwise described herein) in combination with an acid and a salt of chlorite (at a pH of about 6.0-7.0, about 5-6, less than about 4.5-5.0, about 4.0 to about 5.0-6.0) will speed the production of chlorine dioxide and minimize the residual chlorite for maximum effect.

The term "sinusitis" or "chronic sinusitis" (aka rhinosinusitis or chronic rhinosinusitis) is used to describe inflammation of the sinuses that occurs with a viral, bacterial, or fungal infection. The condition may be acute or chronic (chronic sinusitis). In patient free from sinusitis, the sinuses are air-filled spaces in the skull (behind the forehead, nasal bones, cheeks, and eyes) that are lined with mucus membranes. Healthy sinuses contain no bacteria or other germs. Usually, mucus is able to drain out and air is able to circulate. When the sinus openings become blocked or too much mucus builds up, bacteria and other germs can grow more easily and irritating immune factors are released in the area.

Sinusitis can occur as a consequence of any one or more of the following conditions, among others:

Small hairs (cilia) in the sinuses, which help move mucus out, do not work properly due to certain medical conditions;

Colds and allergies may cause too much mucus to be made or block the opening of the sinuses;

A deviated nasal septum, nasal bone spur, or nasal polyps may block the opening of the sinuses.

Sinusitis can be acute or chronic. Acute sinusitis symptoms last about 2 to 8 weeks. Chronic symptoms last much longer, and can last a few months or a lifetime. Acute sinusitis is generally caused by damage to the lining of the sinuses from surgery or infections. Chronic sinusitis is almost always caused by fungi.

The following are risk factors for sinusitis and may guide the person of ordinary skill in determining those subjects or patients at risk for developing sinusitis (subject or patient at risk for sinusitis):

Allergic rhinitis or hay fever;
Persistant colds;
Sore throats;
Asthma;
Children who regularly attend day care;
Patients or subjects with diseases that prevent the cilia from working properly, such as Kartagener syndrome and immotile cilia syndrome.
Patients or subjects who are subjected to changes in altitude (especially activities such as flying or scuba diving)
Patients or subjects with large adenoids;
Tooth infections (although somewhat rare)
Weakened immune system including from HIV, chemotherapy, other.

Symptoms of Sinusitis

The following symptoms shall provide guidance for instituting therapy with the present invention in order to treat or inhibit sinusitis.

The classic symptoms of acute sinusitis in adults usually follow a cold that does not improve, or one that worsens after 5-7 days of symptoms. Symptoms may include any one or more of the following:

Bad breath or loss of smell;
Cough, often worse at night;
Nasal Discharge and congestion;
Fatigue, malaise and generally not feeling well;
Fever or elevated temperature;
Headache—pressure-like pain, pain behind the eyes, toothache, or facial tenderness;
Nasal congestion and discharge;
Sore throat and postnasal drip;

Symptoms of chronic sinusitis are the same as those of acute sinusitis, but tend to be very intense and often last for years.

Symptoms of sinusitis in children include:
Cold or respiratory illness that has been improving and then begins to get worse;
High fever, along with a darkened nasal discharge, for at least 3 days
Nasal discharge, with or without a cough, that has been present for more than 10 days and is not improving.

Evidence of Sinusitis from Physical Examination Include:
Nose polyps;
Signs of inflammation;
Tapping over a sinus area which evidences infection.

It is noted that regular x-rays of the sinuses are not very accurate for diagnosing sinusitis, but viewing the sinuses through a fiberoptic scope (nasal endoscopy or rhinoscopy) may help diagnose sinusitis. Alternatively, a CT scan of the sinuses may also be used to help diagnose sinusitis. If sinusitis is thought to involve a tumor or fungal infection, an MRI of the sinuses may be appropriate.

If a patient has chronic or recurrent sinusitis, other tests may include:
Allergy testing;
Blood tests for HIV or other tests for poor immune function;
Ciliary function tests;
Nasal cytology; and
Sweat chloride tests for cystic fibrosis.

For sinus pain or pressure, in combination with the use of the present invention the following may be additionally appropriate:

Avoid flying when congested;
Avoid temperature extremes, sudden changes in temperature, and bending forward with head down;

In preferred aspects of the invention, sinusitis is treated alone by the present method, without additional therapy. At some point, in limited instances, consideration of prescription medications, antibiotics and/or further testing may be appropriate as adjunct or additional therapy to that of the present invention. In most instances, however, the present invention results in a significantly diminished symptomology associated with sinusitis and in many instances, a complete cure, without requiring additional therapy.

Acute sinusitis should be treated for 7-14 days, about 10-14 days. Chronic sinusitis should be treated for 3-4 weeks. Some people with chronic sinusitis may need special medicines to treat fungal infections.

Surgery to clean and drain the sinuses may also be used, especially in patients whose inflammation returns, despite medical treatment. An ENT specialist (also known as an otolaryngologist) can perform this surgery. Prior to the present invention, most fungal sinus infections required surgery. Surgical repair of a deviated septum or nasal polyps is believed to prevent the condition from returning.

Sinus infections, especially acute and chronic sinusitis may resist all present treatments. Chronic sinusitis is usually not curable. If there are recurrent attacks, a patient should be checked for underlying causes such as nasal polyps or other problems, such as allergies. It is noted that using the present invention, the prognosis for the treatment and cure of sinusitis, especially including chronic sinusitis is excellent, even without surgery or using other medications, an unexpected result.

Complications of Sinusitis

Although rare, complications of sinusitis may include:
Abscess;
Bone infection (osteomyelitis);
Meningitis;
Skin infection around the eye (orbital cellulitis).

Prevention

In addition to gargling or otherwise administering the present invention prophylactically to reduce the likelihood that a patient will contract sinusitis (for example, by treating a cold or sorethroat in the sinus or contiguous membranes with the present invention) or that acute sinusitis will develop into chronic sinusitis, the following approaches may additionally be helpful:

Treat allergies quickly and appropriately; and
Use a humidifier to increase moisture in the nose and sinuses.

The term "sinus" or "sinuses" is used to describe the paranasal sinuses, which include any of the four sets of cavities in the bones adjoining the nose: maxillary, the largest, between the eye socket and the palate and upper jaw; frontal, just above and between the eye sockets; ethmoid, consisting of 3-18 thin-walled cavities between the nasal cavities and the eye sockets; and sphenoid, behind the nasal cavity. All are absent or small at birth, enlarge gradually until puberty, and then grow rapidly. They affect the sound of the voice and may help to warm inhaled air. Their lining produces mucus, which drains into the nasal cavity. Blockage of their outlets by swelling (from allergy or infection), polyps, or structural problems hampers breathing through the nose and can lead to serious infection (chronic sinusitis). Until the advent of the present invention, severe sinus obstruction often required surgery, which had to be done with extreme care in order to avoid harm to nearby brain structures or the eyes. In the present invention, it is the tissue which lines the sinus or is found in proximity to the sinus which is treated using compositions according to the present invention to treat or reduce the likelihood of the occurrence of sinusitis, especially chronic sinusitis.

The term "chlorine dioxide" is used to describe a chemical species, represented as ClO2 having disinfectant properties and being useful in the present invention.

There are several ways of releasing $ClO_2$ into solution. The most suitable for personal or topical use is by mixing sodium chlorite with an acid as pointed out in U.S. Pat. No. 4,084,747 patent. As also described herein, a disproportionation agent can be included in the composition to facilitate and enhance chlorine dioxide formation. This chemistry is now well known and may be applied for use in mouthwashes.

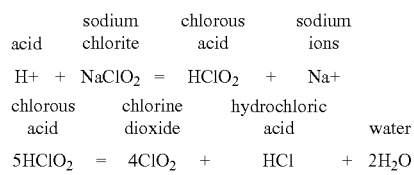

Although a number of acids, including α-hydroxy acids may be used in the present invention, lactic acid is preferred for use in the present invention. US patent (U.S. Pat. No. 5,731,347) by the present inventor, shows that lactic acid is an excellent therapy for canker sores in the mouth, as confirmed in a Phase 2 clinical study. This acid is therefore ideal for use on mucus membranes, as well as for acidifying chlorite. It is the preferred acid for use in the present invention.

Glycerin is often used as a lubricant or coating, among others, to soothe mucus membranes. In U.S. Pat. No. 5,616,347, the present inventor showed that glycerin is one of the few emollients that can be used with chlorine dioxide since it will not be oxidized. Glycerin, then, is an acceptable additive to the chlorine dioxide antiseptic solution. It also tastes good.

Other methods for producing chlorine dioxide are useful in the present invention, but are less than ideal:

Oxidation of chlorite by hypochlorite or bleach

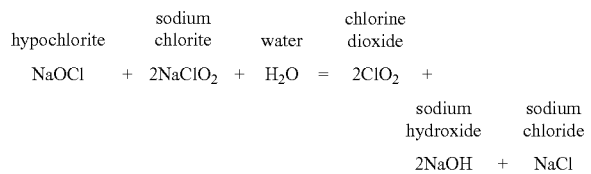

Oxidation of chlorite by chlorine or chlorine compounds:

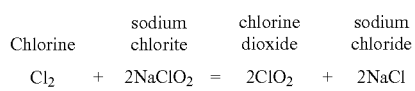

Oxidation of chlorite by sodium persulfate:

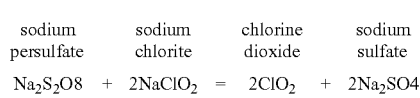

Chlorine dioxide releasing compounds, bleach and chlorine as shown, taste bad and are irritating to mucus membranes. Sodium persulfate is a powder difficult to store and handle. It also irritates mucus membranes. These three chemical activators would not be good choices for applying to sinus membranes in the present application.

The terms "stabilized chlorine dioxide" and "stabilized chlorite" are used synonymously to describe certain formulations which may be used according to the present invention. Stabilized chlorine dioxide products are prepared by buffering sodium chlorite with carbonate or phosphate and hydrogen peroxide. This approach, in reality, stabilizes the chlorite, not chlorine dioxide. Stabilized chlorite is not the same as chlorine dioxide, and does not have the same oxidizing properties. The oxidizing action of chlorite is much lower, and is far less useful. Another main difference between the two compounds is that chlorine dioxide is a gas, and sodium chlorite is a salt. Stabilized chlorine dioxide formulations produce chlorine dioxide with the addition of acid, but because of the buffering incorporated in the compound, a great deal more acid is required to lower the pH to levels which produce appreciable concentrations of chlorine dioxide, and the concentration of chlorine dioxide is generally much less than the preferred compositions according to the present invention. Stabilized chlorine dioxide compositions are clearly less preferred than are the two part compositions of the present invention (which preferably include a disproportionation agent as otherwise described herein) which generate chlorine dioxide contemporaneously, i.e. preferably, in a few seconds and generally, in less than about an hour or so, preferably less than about 30 minutes, less than about 15 minutes, less than about 5 minutes, less than about 1-2 minutes, less than 1 minute before use. It is noted that in compositions which comprise a carbohydrate or sugar disproportionation agent, and in particular, ribose, optionally in combination with a hydroxyl free aldehyde disproportionation agent, may maintain relatively constant chlorine dioxide concentrations for periods of up to 3-4 days, an unexpected result.

In contrast to stabilized chlorine dioxide solutions, to make active chlorine dioxide in the preferred methods, an acid is mixed with chlorite, which slowly releases the gas. The gas is then captured in a solution or gel, preferably in solution. The reaction normally requires high acidity (low pH), but solutions of pH of about 4.5-6.5 (preferably about 5.5 to about 6.5, about 6.0 being more preferable) may be used and will be effective. Compositions according to the present invention may also entail speeding the release of chlorine dioxide at mild acidity (closer to neutral pH) by including a disproportionation agent, especially a hydroxyl free aldehyde disproportionation agent as otherwise disclosed herein. The resulting product is then optimized for use on the body.

The manufacturers of stabilized chlorine dioxide appropriate the term "stabilized" to capitalize on the beneficial properties of chlorine dioxide. The term is somewhat misleading and therefore in the present invention has correctly described stabilized chlorine dioxide as stabilized chlorite, although the term "stabilized chlorine dioxide" may be used to describe these compositions. The "stabilized chlorine dioxide" phrase has become popular by effective marketing. Many people refer to it without knowing the difference, and research papers actually incorporate it incorrectly. The stabilized manufacturers "justify" the misnomer by stating that the term has been in use for some time.

The overall pH range of compositions (where the acid and chlorite salt have been mixed and produced effective amounts (concentrations) of chlorine dioxide for administratikon, for purposes of the present invention is from about 4.5 to about 6.5 or more, more preferably about 5.0 to about 6.5, about 5.5 to about 6.5, about 6.0, about 6.5.

Generally, the concentration of chlorite salt used to generate chlorine dioxide in the present invention represents at least about 0.0005M and preferably ranges from about 0.002M to about 0.5M or slightly higher. In certain preferred compositions which are biocompatible and non-irritating, the amount of chlorite salt comprises at least about 0.0005M and preferably ranges from about 0.002M to about 0.2M. A lower amount of chlorite which is used is preferred because the tendency will be to avoid irritation to the membranes to which the chlorine dioxide containing compositions acceptable for the sinus and contiguous membranes are applied.

The amount of biologically compatible acid, preferably an a-hydroxy acid and more preferably lactic acid or a mixture of lactic acid and another acid added to the chlorite salt is generally that amount effective to provide an initial pH of the reaction mixture (which mixture includes acid and chlorite salt or preferably, acid, chlorite salt and aldehyde, among other components) of below about 6.5-7.5, about 6.0, below about 6.0, below about 5.5, below about 5.0, below about 4.5.

The acid is preferably provided in a concentration of about 0.00005M to upwards of about 0.01M, depending upon the final pH of the solution desired, which in the present invention requires biocompatability. In certain preferred compositions, the concentration of acid preferably ranges from about 0.01M to about 0.2M, depending upon the amount of chlorite in the composition, which will create a balance of pH.

In certain compositions according to the present invention, the chlorite salt is combined with the acid preferably at about 15° C. to about 30° C. (in most instances, ambient temperature or a warm water bath) to produce chlorous acid. Thereafter, the chlorous acid is left to disproportionate to chlorine dioxide. In general, the disproportionation step is carried out in the same aqueous medium where the formation of chlorous acid occurs. The temperature of the disproportionation step may vary, but will generally range from about 15° C. to about 30° C. or higher. After production, the chlorine dioxide solution may be used directly or diluted by adding water, depending upon the route of administration e.g., gargle, nasal spray, steam inhalation, etc. as otherwise described herein. In certain preferred aspects of the invention, wherein chlorine dioxide is produced from chlorite, acid and a disproportionation agent, preferably a hydroxyl free aldehyde disproportionation agent, the concentration of chlorine dioxide produced may be maintained constant for a period up to about 3-4 days.

In alternative compositions, the use of a disproportionation agent, preferably in the form of a hydroxyl free aldehyde chemical composition, enhances and hastens the production of chlorine dioxide from chlorous acid. In this aspect, either before, during or after the formation of chlorous acid, an effective amount of an agent for disproportionating chlorous acid to chlorine dioxide is added to the solution. While the disproportionation agent may be added after the formation of chlorous acid, preferably the disproportionation agent is already present in the acid solution when the acid solution is combined with the aqueous mixture of chlorite salt, in order to produce effective amounts of chlorine dioxide. The inclusion of the disproportionation agent does not appreciably affect the pH of the initial solution which includes acid and chlorite salt, because the aldehyde or the carbohydrate (sugar, including ribose) is a neutral species. By combining the aldehyde disproprotionation agent initially with acid and chlorite salt in this way, as soon as chlorous acid is generated, the disproportionation reaction is enhanced. The overall result will be to shift the equilibrium toward more chlorous acid generation and consequently, more chlorine dioxide formation. Using a disproportionation agent, at least 10% and generally at least about 30-40% up to about 80% or higher of chlorite ion is converted to chlorine dioxide and chloride ion. In the absence of a disproportionation agent such as a hydroxyl free aldehyde disproportionation agent, the conversion is significantly slower and is less efficient. The significant enhancement of chlorine dioxide production and the limitation in residual chlorite ion using a hydroxyl free aldehyde disproportionation agent results in compositions which can be effectively administered to sinus or surrounding tissues in treating/inhibiting sinusitis or reducing the likelihood that a patient or subject at risk for sinusitis will contract sinusitis. This is an unexpected result.

It is noted that in this aspect of the present invention which utilizes a hydroxyl free aldehyde disproportionation agent to enhance chlorous acid disproportionation to form chlorine dioxide and minimize residual chlorite, any acid which produces an initial pH in the reaction mixture of less than about 5.0-6.0, preferably 4.5 or lower (about 4.0 to about 5.5 being preferred) may be utilized. Numerous acids may be used in the present invention to generate chlorine dioxide including a variety of organic acids, for example, citric, propionic, fumaric, glycolic, lactic, malic, tartaric and acetic, among others with lactic acid or a mixture of lactic acid and another acid, being preferred.

Administration of Compositions

The presently described compositions may be administered by any route of administration which results in effective amounts of chlorine dioxide being delivered to the membranes of the sinus or contiguous membranes (such as the upper reaches of the nasal cavity and tissue at the back of the throat) which adjoin the sinus. Thus, compositions for use in the present invention comprise, an effective amount of chlorine dioxide, and, in most instances, residual acid, a residual salt of chlorite, a disproportionation agent and/or a by-product of the production of chlorine dioxide from these components and optionally, flavoring agents (e.g. peppermint and menthol, among others), wetting agents (e.g. Stepan Bioterge, Polysorbate 80, etc.), coating agents (e.g., glycerin and polyethylene glycol), mucus looseners, such as sodium carbonate/sodium bicarbonate and/or guaifenesin to loosen the mucus on the exposed membranes which may be safely (i.e., without appreciable irritation or other untoward effects) delivered to the patient, among other optional components.

The compositions used in the present invention are formulated to be delivered to the sinus and adjoining tissue, including the upper reaches of nasal cavity and the mouth. The compositions are administered to the affected membranes (sinus membranes and membranes adjoining the sinus, including the nasal cavity) in order to inhibit, eliminate or reduce the likelihood of infection (including treating, inhibiting or reducing the effect of colds and/or sore throats in the sinus tissue or tissue contiguous to the sinuses) and consequently to treat or inhibit sinusitis in a patient or reduce the likelihood of a patient either contracting sinusitis in the first instance, for example, by having a throat infection travelling to the sinuses or having acute sinusitis develop into chronic sinusitis. It has been discovered quite unexpectedly that effective amounts of chlorine dioxide delivered to the sinus and contiguous membranes of a patient may treat, inhibit and/or reduce the likelihood of acute or chronic sinusitis especially including without additional antimicrobial agents and in the absence of prior art surgical practices to alleviate the symptomology associated therewith. In still other limited instances, the present method may be combined with one or more antibiotics or antifungal agentsand/or surgery to enhance the therapy.

The route of administration to effect the present method may be oral (by gargling), by inhalation (e.g. by nose or mouth inhaler, or steam inhalation) and/or by the administration of nose drops, nasal spray or liquid lavage, among others. In preferred aspects of the invention, the composition is administered first by gargling, following by administering the compositions by nasal spray, inhalation and/or nasal lavage. Compositions may be administered for example, by having the patient or subject gargle with an appropriate composition in a manner which results in sinus, nasal passages and contiguous membranes, especially including infected sinus membranes, being exposed to effective amounts of chlorine dioxide. Mouth inhalers and/or nose inhalers may be formulated to facilitate the introduction of chlorine dioxide onto sinus membranes or contiguous membranes such as the upper roof of the mouth and or upper reaches of the nasal cavity. The use of nose drops, nasal spray or liquid lavage also may be used to introduce chlorine dioxide to infected tissue or tissue which may become infected. Various routes of administration may be chosen to maximize the delivery of chlorine dioxide to the tissue which is desired to be treated and/or protected.

Regardless of the route of administration of chlorine dioxide containing compositions, acute sinusitis usually should be treated for about 1 day or longer, preferably about 1-15 days. Clearing and symptom reduction and elimination will be evidence. Since spores may remain in the sinuses for a few days, chronic sinusitis treatment may take several days. If infection is again transferred from the troat or a cold, sinus treatment may need to be repeated. The return of symptoms or relapse is relatively obvious from the commonly encountered stuffiness or running nose. The present invention can be used continuously if spore infusion and/or symptoms, returns. Chronic sinusitis is treated for a period which tends to be longer than the treatment regimen for acute sinusitis, and is at least about 2 days to several months, preferably for at least about 1 week, at least about 2 weeks and in many instances for 3-4 weeks or longer. It is noted that in many instances, the chlorine dioxide compositions are the sole agents which are required to effectively treat the sinusitis. It is noted that the use of the present invention preferably occurs in the absence any other therapy.

In preferred aspects, the present invention can be used to treat sinusitis, especially including chronic sinusitis. It is an unexpected result that the present methods of treatment with chlorine dioxide containing compositions according to the invention may be used to treat sinusitis, including chronic sinusitis, in a relatively short time and incorporating a relatively easy procedure considering the need in the past for utilizing decongestants, antibiotics, anti-inflammatory agents and/or surgery.

Methods of Irrigating the Nasal Passages

As described, chlorine dioxide compositions may be administered to a patient by exposing sinus tissue and tissue contiguous to sinus tissue in the upper mouth and/or throat or the far reaches of the nasal cavity to effective amounts of chlorine dioxide, orally (for example by garling with mouthwash), by inhalation (including nasal inhalation) or by nasal spray or drops. A good substitute for the nasal spray is a liquid stream lavage. In this approach, the chlorine dioxide solution is fed by gravity or slight pressure into one nostril and the composition exits the other. The treatment, sometimes called "neti pot," usually produces fast results. The concentration of chlorine dioxide may also be lowered to about half that which is used in the nasal spray.

Aeorosol machines are able to substitute for spraying compositions into the nose and onto the sinus and contiguous/adjacent membranes by emitting a mist or chlorine dioxide vapor from steam vaporizers or humidifiers. However, chlorine dioxide may produce irritation in the lungs in large enough quantity or time of exposure. Since most of the moist air hitting the nose in this case is probably gas, people breathing the vapor would need to be careful to notice any lung irritation. For the present, breathing the vapor should be limited to about 15 seconds or less. This method also proves useful in the treatment of asthma.

As discussed, the present invention is especially useful in the case of chronic sinusitis which is difficult to treat and may be a lifelong illness. Since sinus inflammation or infection may affect all parts of the greater oral cavity, researchers and physicians now refer to the disease as "chronic rhinosinusitis." The best treatment method, therefore, utilizes both gargling in the mouth and throat, as well as, spraying or irrigating the nose where some of the liquid enters the sinus passages. Either gargling or spraying alone can be effective, depending upon the site of the infection, and the seriousness of the disease.

Sinusitis can be allergic or non allergic, microorganism caused or non infectious, chronic or acute. The cause is often baffling, and many times the treatment is non responsive. The present invention shows that chlorine dioxide antiseptic in a non irritating concentration can reduce or eliminate the inflammation and infection in nearly all of these cases whatever the cause.

This surprising global efficacy is due at least in part to the wide spectrum of bacterial and viral kill by chlorine dioxide, as well as its ability many times to oxidize and neutralize the body's irritating immune response. This response comprises active immune factors such as inflammatory cytokines, enzymes, and oxygen radicals. Eosinophil peroxidase, for example, a white blood cell formation, is probably neutralized by chlorine dioxide oxidation. The importance of this action is obvious in that, aside from the peroxidase killing invading fungus cells, which was nature's purpose, the enzyme is involved in mucus membrane attack and probably the illnesses of 35 million chronic fungal sinusitis patients.

In vitro, the chlorine dioxide solution will kill most microorganisms in about one minute, including gram negative bacteria, fungal spores, and viruses, which elude most other disinfectants. It is surprising that chlorine dioxide as one of the fastest known biocides is also non toxic or non-irritating to the mucus membranes.

Chlorine dioxide solution can be used routinely, and is relatively easy to apply by gargle and spray, as described hereinabove. The progression of rhinosinusitis infection or inflammation can be halted at the first sign of the disease, as well as after the illness has progressed. Colds and flu infection may likely be prevented in the first place with daily mouthrinse/gargling. This is reasonable considering that all viruses are deactivated in seconds (in bench type tests), and the active chlorine dioxide molecule is quite penetrating.

In addition, chlorine dioxide will remove biofilms, a sticky coating of bacteria that is fairly impervious to other antiseptics. Biofilms are found to coat the passages of fungal sinusitis patients, complicating therapy.

The application of the present invention promises to obviate enormous morbidity due to colds, sore throats, as well as sinusitis.

EXAMPLES

To treat sinusitis, sore throat or a cold, one aspect of the present method is directed to gargling the throat with antiseptic $ClO_2$ solution, i.e. a $ClO_2$ mouthwash, and then following up the gargling (within a period of no more than several hours, and preferably just after gargling) with spraying each nostril with the solution. The total nasal/oral airway then will be cleared of most microoganisms at the same time, and very likely, many offending immune cells. The nasal passages will start to drain quickly after treatment. An infection will produce a tingle or burning sensation after application for 5 or 10 seconds.

The application time and approximate quantities in a preferred embodiment are exemplified as follows:

1. One cup is filed with about 15 ml of Part A, which comprises essentially a solution of sodium chlorite, and another cup with acid solution (preferably containing a disproportionation agent, such as a sugar, in particular, ribose), Part B, 15 ml. Make sure the levels of liquid are at least approximately the same in each cup. Other components consistent with the therapy, used in the composition and stableto chemical conditions during storage may also be added to Part A and/or Part B.
2. One cup is poured into the other, mixed and allowed to sit for a period of about 15 seconds or so. The concentration of chlorine dioxide after this period will be about 15 ppm or so.
3. The patient or subject gargle about ⅓ the volume of the cup, or about 10 ml, as far back in the throat as possible for about 10-30 seconds, about 15 seconds or so. With head back, the solution is gargled so that it rinses high in the throat, at the entrance of the nose, and if possible, the solution is allowed to enter the back of the nose.
4. After a few minutes, a 10 ml gargle is repeated for about 15 seconds. The $ClO_2$ concentration will now be higher, e.g., about 25 ppm or so from the same solution in the cup. This time the nasal passages will be a little clearer as gargling proceeds due to the action of the first rinse.
5. The rest of the cup is poured into a small nasal sprayer, which is preferably supplied. Each nostril is sprayed 5 or 6 times, the patient or subject breathes in briskly, holding the opposite nostril closed.
6. After a few minutes, the spray procedure is repeated; there will probably be enough liquid solution left in the spray bottle for further treatments. Liquid left in the spray bottle is usable for about 3 days.

Nasal passages may drain for 5-10 minutes or more after treatment. In about ½ hour, if nose and sinuses are not completely clear, repeat the above gargle and spray procedure, as described above.

The total time taken for the gargle and spray is about 10 minutes. The purpose of gargling twice for 15 seconds, rather than once for 30, is that it is difficult for most people to gargle vigorously for more than 15 seconds. Also the time delay between the two rinses permits the nasal passages to clear and be open to the antiseptic action the second time.

It is best to treat a cold or influenza at the first sign of an irritation in nose or throat. Entrenched colds and sore throats, although showing immediate relief, usually need chlorine dioxide treatments for several days. Flu and bronchitis are more difficult to treat after becoming internalized.

Discussion

By experimenting many times when gargling with a $ClO_2$ mouthwash and related formulations, it was noticed that sore throats were relieved. If an infection was present, there was a slight burning for about 5 seconds which then subsided. The original throat pain at the infection site was much relieved in a few minutes. After a degree of experimentation with the mouthwash, the the present inventor accidentally swallowed some mouthwash, and further, by vigorously gargling, eventually got solution into the back of his nose. To the inventor's astonishment, his sinuses cleared, and soon he discovered that a surprisingly low concentration of chlorine dioxide was able to clear mucus from the nasal passages. Somehow the small amount of chlorine dioxide solution or vapor, or possibly the chlorine dioxide vapor alone, was quite penetrating. Increasing the number of treatments but with low doses was able to produce good results.

After realizing that infections anywhere in the respiratory tract were interrelated, and the same microorganisms could be found elsewhere in the mouth, throat or sinuses, it became important to treat infection in all respiratory areas. If not treated in this way, infection might linger, or reinstate at the very same place, or establish itself in another part of the airway. The flu infection starts in the nose, for example, but in a few days finds its way elsewhere.

Since therapy was to be performed on those with sinus problems, the inventor needed to find a $ClO_2$ concentration that was effective but definitely not irritating. The application of a strong antiseptic deep into the nasal passages was a little unusual, and unlike the tissue or mucus membranes elsewhere on the body, the sinuses could not be rinsed in an emergency.

Experimenting with various methods of application and concentrations, the inventor found that gargling first for about 30 seconds, so that the mouthwash rinsed, or even entered, the entrance to the back of the nose, was the first valuable step. The treatment was improved further, and often absolutely necessary, by following up the gargle with a nasal spray. A variation of the mouthwash was placed into a small standard nasal spray bottle, and each nostril was sprayed while briskly breathing in at the same time. Again, with infection present, there was mild burning for a moment. With a bad infection, a burning was felt deeper in the nasal passages. The stuffy nose, caused by a cold or sinus infection, would drain, often for many minutes with a long standing sinus disease. After the nasal passages were clear or mostly clear, it was easy enough to repeat the operation. With the final concentrations and rinse formulas determined, in no case was there a lingering irritation.

Instead of a spray, other methods of getting chlorine dioxide into the nose and sinuses also produced good results, for example by using chlorine dioxide in a steam vaporizer, or humidifier. A water stream lavage (e.g. "neti pot") forced into a nostril by gravity was useful also, although a lower concentration of chlorine dioxide was necessary in the water solution to prevent irritation.

The entire treatment process is a matter of minutes and nasal passages remain clear. The speed of response may simplify clinical studies. Ordinary rhino-based acute colds and sore throats seemed to respond to the $ClO_2$ particularly fast, and it is suggested that the oxidation of interleukin 8, a cytokine that causes cold symptoms (an immune response cell) may be one reason for the prompt response. These cytokines and others are involved in all types of sinusitis, and also play an important role in mucosal thickening. The invention appeared to be most efficacious when applied at the onset of symptoms. If an infection were already internalized many days as often happens with the flu or bronchitis, the healing effect of the rinse and/or spray is perhaps better described as an inhibitor of symptoms rather than providing complete relief or a cure. On the other hand, when treating the more serious chronic sinusitis, involving clogged nasal passages and apparent infection, surprisingly, most major symptoms are promptly relieved, in most instances without antibiotics, antifungal agents and/or surgical approaches.

As discussed hereinabove, the chronic forms of rhinosinusitis are often mediated by many contributing factors, including a wide range of microorganisms, allergens, and immune responses. In experiments with chlorine dioxide through the years the present inventor discovered another exceptional property of $ClO_2$—the ability to oxidize and neutralize enzymes, and cytokines (see Kenyon and Douglas). Interestingly, this kind of chemical reaction was first noticed when experiencing a quick reduction of pain on applying chlorine dioxide to a bad sunburn or hornet sting. The body's reaction was the cause of pain, and this was chemically neutralized. Active compounds released into a wound by the immune system help cure infection, but many times an overreaction causes pain and attacks tissue. Chlorine dioxide reacts with other oxidizing agents in an oxidation/reduction process, and likewise will neutralize hydrogen peroxide, free radicals, and other highly active oxygen molecules the body produces as part of the immune response.

The tissue in mammalian bodies is protected from indigenous oxidants like peroxide, the hypochlorite ion, and superoxide, by many internal reducing agents such as catalase and glutathione, and also by nutrients such as vitamins and minerals, which are also reducing agents. These tissues and cells appear to be protected from topically applied chlorine dioxide by the same mechanism. Microorganisms do not incorporate these reducing nutrients and are easily oxidized. Bacterial cell walls and viral envelopes, further, don't have the same chemical constituents as our own cell walls, and break apart immediately in response to $ClO_2$ (see EM photos of bacteria cell splitting).

Chronic sinusitis harbors many kinds of immune cells. For example, allergic sinusitis or rhinitis—mostly non infectious, presents its own band of immune cells. Whether allergic or non allergic, many of the biochemical responses to sinusitis are reduced or eliminated by the $ClO_2$ treatment since the familiar symptoms, headache, itchy nose, stuffed passages, etc, are gone or greatly reduced in a matter of minutes. It is of interest that ordinary saline sprays provided improvement in chronic sinusitis (29, 30), and other research has shown that a reduction of immune response factors was possible by purely mechanical means. In one study, "Nasal Hypothermia and Simple Irrigation for Perennial Rhinitis. Changes in Inflammatory Mediators." Chest. 1994, Georgitis, J W, saline sprays "significantly reduced levels of leukotriens and histamines." It would appear that ordinary sprays and irrigation are contacting infected parts of the sinuses (31), and physically removing immune cells. Chlorine dioxide sprays do it substantially better with the addition of chlorine dioxide as a neutralizing factor.

A subset of chronic sinusitis, in particular, allergic fungal sinusitis, AFS, is not due to an infection per se, but to a reaction to environmental fungi finely dispersed into the air. The ubiquitous nature of these airborne spores may continuously sensitize those affected, as might, a many year infection produced by fungus of the toenail. It is now understood that allergy to fungus produces in important part, the long standing and difficult to cure chronic sinusitis disease. Scientists supported by the NIH discovered that people with chronic sinus inflammation have an exaggerated immune response to common airborne fungi, Alternaria, Aspergillus, and Penicillium, and an estimated 37 million people in the U.S. suffer from this chronic sinusitis. Antibiotics, in most cases, are ineffective because they target bacteria, not fungus. AFS treatment may require wide debridement of the affected areas and a long period of anti fungal oral medication. Unfortunately, recurrence is not uncommon once the disease is removed. Chronic allergic fungal sinusitis was first described in 1981 by Millar, but for some time was not fully recognized.

While not being limited by way of theory, the chlorine dioxide used in the present invention probably acts on the allergens themselves. In vitro chlorine dioxide will kill, and presumably neutralize, all fungal spores in two minutes. It seems, however, that the massive symptomatic relief provided by the current invention can not be explained by this attribute alone. Users of the invention have noted near-immediate reductions in inflammation and discomfort. Chlorine dioxide is likely interacting with the body's immune response itself.

The rapid reduction of symptoms and disease when encountering non infectious or chronic allergic sinusitis is probably due to the elimination of eosinophils released into the sinuses. The eosinophil is a white blood cell developed by nature to remove larger organisms than bacteria, and is triggered in response to an allergen like dust, pollen, and cigarette smoke. As is now well published, the fungal spore can elicit a strong immune response from the eosinophil. The overactive response due to continuous sensatization causes damage to the airway mucosa and produces thick mucus. A recent New York study (17) shows that "chronic sinusitis sufferers with high levels of respiratory mucus eosoniphils have more frequent sinus infections and surgical procedures, take more antibiotics and fungal medications, are more likely to suffer from asthma and nasal blisters called polyps, and are less likely to be helped by any treatment." According to *Eosinophils, Chronic sinus Infections & Asthma*, 2005, by Gabe Mirkin, M.D., "Having many eosoniphils means that the asthma and sinusitis is usually not curable and often difficult to control." *The American Academy of Allergy, Asthma and Immunology* states that "the approach to managing non infectious sinusitis remains controversial."

Chlorine dioxide may remove eosinophils by three separate mechanisms: inactivating the offending fungal spores, removing the mediating or activating cytokine, and/or by targeting the chemistry of the eosinophil itself. The chemical basis by which the eosinophil produces tissue damage and microbial inactivation is now known (20, 21). It is due to the formation of a highly active eosinophil peroxidase enzyme, and possibly other oxidant species such as super oxide. These compounds attack both the fungus and unfortunately, the mucus membranes of the sinuses. The biochemical construction of the peroxidase takes place by involving chemical intermediates, tyrosine, hydrogen peroxide, and bromide, all theoretically oxidized or reduced by chlorine dioxide.

Of further interest, as reported in the last few years, sinusitis infection may be complicated with biofilms. This sticky bacterial layer protects microorganisms from being killed or removed by antibiotics or washed by solution. In one study, biofilms were present on the tissue of 80% of patients undergoing surgery for chronic sinusitis (5). Chlorine dioxide has been used for many years in commerce and industry as a biofilm remover, dissipating bacterial films (sometimes called slime) from water towers, pipe lines, and heat exchangers. The chlorine dioxide molecule makes an excellent penetrant. It is a gas, a small energetic molecule, non ionic, and highly soluble in both water and oil—properties suitable for penetrating mucus as well as biofilms. Now, using the present invention, biofilm removal in nasal passages as an aid in treating chronic sinusitis is possible.

There are many reports, especially from CDC and NIH that chlorine dioxide kills all flu viruses, in vitro, in a few seconds (see CDC and NIH). This confirms other studies of chlorine dioxide in which all viruses tested are inactivated within a minute. According to Josephson in *Sinus Relief Now*, "When treating acute sinusitis and rhinosinusitis, unfortunately, there are no medicines today that fight viral sinus infections. The decongestants, cough suppressants, and fever/pain medications will only make you feel more comfortable through the healing phase." However, with the present invention, gargling and spraying with chlorine dioxide compositions at the first sign of a cold or respiratory infection would immediately stop the spread of infection, and prevent setting the stage for further intrusion or obstruction of the nasal passages. Routinely gargling once or twice a day with chlorine dioxide mouthwash would likely prevent a flu infection in the first place, or the onset of a cold or sore throat. In the Paper, "Protective effect of low-concentration chlorine dioxide gas against influenza A virus infection," Ogata and Shibata, *J Gen Virol*, 89. 2008. H1N1 and other flu viruses take 2-3 days after initial infection in the throat/nasal cavity to proliferate and develop characteristic symptoms.

Despite the importance of chronic sinusitis, few if any controlled clinical trials of medical management have been performed. From *Chronic Sinusitis,* 2008, by Gabe Mirkin, M.D., "Nobody really knows how to treat sinusitis. Allergy injections are almost always a waste of time, unless you get a stuffy nose every spring and fall—and multiple efforts to treat sinusitis with long term anti-fungal medications have failed." Chronic sinusitis patients often receive antibiotics and prednisone (a cortisone analog) treatments for a month, followed by saline solution irrigations, intranasal steroids, and possibly oral decongestants—and they don't always respond (22, 25). The present invention reflects the discovery that by addressing the causes of sinusitis and sore throat, and utilizing chlorine dioxide in a gargle and as a spray, preferably in combination, the presenting symptoms of the disease are removed better than with antihistamines and decongestants, as well as the disease itself.

The present invention promises to be a significant advance in treating and curing sinus, nose, and throat illness. Moreover, according to the NIH, "Health experts have suggested that chronic sinusitis and asthma may be the same disease manifested in two parts or the respiratory system."

The invention claimed is:

1. A method of treating, inhibiting or reducing the likelihood of sinusitis in a patient or subject comprising administering to said patient or subject a composition consisting essentially of an effective amount of chlorine dioxide within the range of 7.5 ppm to 50 ppm.

2. The method according to claim 1 wherein said composition consists essentially of 10 ppm to 30 ppm chlorine dioxide.

3. The method according to claim 1 wherein said composition consists essentially of 7.5 ppm to 25 ppm chlorine dioxide.

4. The method according to claim 1 wherein said composition is administered to said patient or subject by exposing membranes of the sinus, nasal cavity and upper mouth to said composition.

5. The method according to claim 1 wherein said composition has a pH ranging from 4.0 to 6.5.

6. The method according to claim 1 wherein said composition is adapted for oral administration by gargling.

7. The method according to claim 1 wherein said composition is adapted for nasal administration.

8. The method according to claim 1 wherein said composition is adapted for use as an aerosol.

9. The method according to claim 1 wherein said composition is adapted for use in a humidifier or steam inhaler.

10. The method according to claim 1 wherein said sinusitis is acute sinusitis.

11. The method according to claim 1 wherein said sinusitis is chronic sinusitis.

12. The method according to claim 1, wherein nasal and mouth tissue of the patient or subject is also exposed to the composition in order to reduce the likelihood of a recurrence of sinusitis from a cold or sore throat.

13. The method according to claim 1 wherein said patient or subject is at risk for sinusitis because of allergies, asthma or the age of the patient or subject.

14. The method according to claim 1 wherein said composition is adapted for use as a nasal spray.

15. The method according to claim 1 wherein said composition is adapted for use as a nasal inhaler.

16. The method according to claim 1 wherein said composition is adapted for use as a nasal lavage.

17. The method according to claim 1 wherein said composition further consists essentially of at least one agent selected from the group consisting of flavoring agents, wetting agents, mucus loosening agents, membrane coating agents, decongestants and mixtures thereof.

18. The method according to claim 17 wherein said mucus loosening agent is sodium carbonate, sodium bicarbonate, guaifenesin or mixtures thereof.

19. The method according to claim 17 wherein said membrane coating agent is glycerin.

20. A method of treating or inhibiting sinusitis according to claim 1 in a patient or subject, wherein said chlorine dioxide is produced by combining a first aqueous solution consists essentially of an acid and a disproportionation agent and a second aqueous solution consists essentially of a salt of chlorite, said composition, after combining said first and second solution, having a pH of 4.0 to 6.5, wherein said chlorine dioxide is produced at a concentration ranging from 7.5 ppm to 50 ppm.

21. The method according to claim 20 wherein said chlorine dioxide is produced at a concentration of 10 ppm to 30 ppm chlorine dioxide.

22. The method according to claim 20 wherein said composition further consists essentially of at least one agent selected from the group consisting of flavoring agents, wetting agents, mucus loosening agents, membrane coating agents, decongestants and mixtures thereof.

23. The method according to claim 22 wherein said mucus loosening agent is sodium carbonate, sodium bicarbonate, guaifenesin or a mixture thereof.

24. The method according to claim 20 wherein said acid is selected from the group consisting of citric, fumaric, glycolic, lactic, maleic, malic, tartaric, mandelic, sodium bisulfate, potassium bisulfate, phosphoric acid and mixtures thereof.

25. The method according to claim 20 wherein said acid is lactic acid or a mixture of lactic acid and at least one additional acid.

26. The method according to claim 20 wherein said disproportionation agent is a hydroxyl free aldehyde and said pH is 4.5 to 6.5.

27. The method according to claim 20 wherein said chlorine dioxide is produced at a concentration of 7.5 ppm to 25 ppm.

28. The method according to claim 20 wherein said disproportionation agent is selected from the group consisting of acetaldehyde, cinnamic aldehyde, propionaldehyde or a mixture thereof and said pH is 5.0 to 6.0.

* * * * *